United States Patent [19]
Kiyota et al.

[11] Patent Number: 5,861,092
[45] Date of Patent: Jan. 19, 1999

[54] NITROGEN OXIDE DETECTOR

[75] Inventors: Fumio Kiyota; Masaharu Hasei; Yukio Nakanouchi, all of Kumagaya, Japan

[73] Assignee: Riken Corporation, Tokyo, Japan

[21] Appl. No.: 932,490

[22] Filed: Sep. 18, 1997

[51] Int. Cl.$^6$ ................................................. G01N 27/26
[52] U.S. Cl. ..................... 205/781; 204/425; 204/427; 73/23.2; 73/23.21
[58] Field of Search ................... 204/424–427; 205/781; 422/94, 98; 73/23.2, 23.21

[56] References Cited

U.S. PATENT DOCUMENTS

| | | | |
|---|---|---|---|
| 4,927,517 | 5/1990 | Mizutani et al. | 204/425 |
| 5,217,588 | 6/1993 | Wang et al. | 205/781 |
| 5,476,001 | 12/1995 | Hoetzel et al. | 73/23.31 |
| 5,554,269 | 9/1996 | Joseph et al. | 205/781 |
| 5,763,763 | 6/1998 | Kato et al. | 205/781 |
| 5,780,710 | 7/1998 | Murase et al. | 205/781 |

FOREIGN PATENT DOCUMENTS 0517366  12/1992  European Pat. Off. .

OTHER PUBLICATIONS

Patent abstracts of Japan, vol. 16, No. 421 (P–1414), Sept. 4, 1992 & JP 04 142455A (Osaka Gas Co. Ltd.).

*Primary Examiner*—Bruce F. Bell
*Attorney, Agent, or Firm*—Bachman & Lapointe, P.C.

[57] ABSTRACT

A method and a detector for detecting nitrogen oxide in test gas are provided wherein test gas which contains NOx and interference gases is supplied through an oxygen feeder 4 into a measuring chamber 1a, and the interference gases are oxidized by oxygen or oxygen ion supplied to the measuring chamber 1a through oxygen feeder 4. A total amount of NOx in the test gas is detected based on a level of EMF produced between a first electrode 2 for detecting oxygen and NO2 gas and a second electrode 3 for detecting oxygen.

16 Claims, 1 Drawing Sheet

NITROGEN OXIDE DETECTOR

FIELD OF THE INVENTION

This invention relates to a gas detector, in particular, to a detector for accurately detecting nitrogen oxide in combustion gas.

PRIOR ART

With recent further aggravation of a problem on environmental pollution, it has become increasingly necessary to detect NOx gas in various exhaust gases. Prior art methods for measuring nitrogen oxide includes Saltzman reagent method, Jacobs method, detector tube method and method for automatically analyzing and recording nitrogen oxide. In Saltzman reagent method, dinitrogen tetroxide is colored as nitrous acid, and measured by spectral photometer or photoelectric colorimeter for colorimetry. Jacobs method is different from Saltzman reagent method in that the former utilizes lye as absorption liquid. The automatic analyzing and recording method includes a process for continuously recording colored degree of dinitrogen tetroxide in Saltzman reagent method. The detector tube method is regulated under Japan Industrial Standards (JIS) K0104. In this way, these prior art detecting methods are defective in requiring their complicated and expensive apparatus so that they can neither directly be inserted into exhaust gas pipes for continuous monitoring of NOx gas, nor be mounted in a vehicle with an engine.

For that reason, it is now requested to develop solid-state NOx sensor of small size and inexpensive in manufacture so that they can directly be inserted into an exhaust gas pipe for continuous monitoring of NOx content in the exhaust gas. Some types of new solid-state NOx sensors have been studied, however, no practical type thereof has not yet been developed. For example, as shown in Japanese Patent Disclosure No. 4-142455, solid-state NOx sensors of studied stage have been proposed which comprises an ion conductor, an auxiliary electrode of nitrate attached to the ion conductor and a reference electrode provided in the ion conductor for exposure to atmospheric air thereby to measure electromotive force (hereinafter referred to as "EMF" ) generated produced between the auxiliary and reference electrodes. Also, a new type of such sensors has been reported wherein both electrodes are exposed to a same atmosphere of test gas for simplification of its structure. However, these sensors are disadvantageous in having its lower heat resistance because the auxiliary electrode utilizes nitrate of its melting point at a temperature of 450° C. as an upper temperature limit. In addition, nitrate has its defects in that it is extremely deteriorated by moisture and indicates unstable property for a long duration.

In another aspect, a semi-conducting sensor has been invented with various oxides which have their semi-conducting characteristic for variable electric conductivity. Specifically, in such a semi-conducting sensor, when NOx gas contacts an oxide, it is mainly adsorbed to a surface of the oxide, thereby to cause change of electric conductivity in the oxide, however, the sensor represents its fault in that an output of the semi-conducting sensor rapidly decreases with deterioration of chemical adsorption of gas at a temperature over 500° C. The inventors previously proposed a NOx sensor of electromotive type which includes detection electrodes of various kind of oxides, and it has been found that some oxide of spinel structure is effective for improvement in the selectivity for $NO_2$ gas. Such a NOx sensor of electromotive type is very advantageous in that it may be formed in its flat size with its simplified structure, and moreover is effectively operable in a temperature range from 500° through 700° C. In addition, it has enough selectivity for NO or $NO_2$ sole gas with the detection electrode of an appropriately selected oxide.

However, it has also been found that there is a likelihood that the selectivity of an oxide electrode in such NOx sensors of electromotive type may inconveniently be interfered with hydrocarbon gas. Moreover, the generated EMF is changed in a reverse direction when NO and $NO_2$ gases contact an electrode formed of specific kind of oxides in such a NOx sensor. Thus, a problem may occur that co-existent gases of NO and $NO_2$ interfere with each other to thereby give rise to a harmful effect on detection of test gas.

As gas sensor of semi-conducting type shown in Japanese Patent Disclosure No. 5-157715 removes reducing gases contained in test gas by burning and oxidizing the reducing gases with oxygen supplied through an oxygen pump upon detection of nitrogen oxide in test gas. In detail, in this gas sensor, test gas is introduced through a path into an oxidizing chamber in an encasement of the sensor and oxidized by molecular oxygen supplied to the oxidizing chamber through the oxygen pump which comprises solid electrolyte. Subsequently, the test gas is transported from the oxidizing chamber through a catalytic layer to a measuring chamber wherein nitrogen oxide is detected by a non-selective nitrogen oxide sensor of $SnO_2$ resistance type or SAW (Surface Acoustic Wave) type.

However, the non-selective nitrogen oxide sensor of this type has its demerits in that it is susceptible to characteristic change by variation of oxygen concentration so that electric resistance of the sensor fluctuates with activated adsorption and desorption of oxygen and that it produces characteristic change at an elevated temperature. In addition, as the sensor must be disposed in an atmosphere of constant oxygen content, it requires at least an auxiliary device for controlling oxygen content in the atmosphere. Accordingly, it is apparent that the gas sensor shown in Japanese Patent Disclosure No. 5-157715 needs its complicated structure to accurately detect existence of nitrogen oxide and the characteristic change of the gas sensor should be improved.

An object of the present invention is to provide a detector for detecting nitrogen oxide without interference or any harmful effect to the detection of test gas by co-existent gas.

Another object of the present invention is to provide a detector which can accurately detect nitrogen oxide at an elevated temperature.

Still another object of this invention is to provide a nitrogen oxide detector of simple construction so that it can directly be inserted into a pipe of exhaust gas.

SUMMARY OF THE INVENTION

The method for detecting nitrogen oxide according to the present invention comprises the steps of supplying, into a measuring chamber, test gas that contains NOx and at least an interference gas; oxidizing the interference gas and NO gas in the test gas by oxygen or oxygen ion supplied to the measuring chamber through an oxygen feeder; and detecting a total amount of NOx in the test gas based on a level of EMF generated between a first electrode for detecting oxygen and $NO_2$ gas and a second electrode for detecting oxygen. Because the interference gas is oxidized by oxygen or oxygen ion, the total amount of NOx can accurately be detected based on EMF produced between the first electrode for detecting oxygen and $NO_2$ and the second electrode for detecting oxygen without harmful influence by interference gas.

In an embodiment of the invention, the invention's method may comprise defining the measuring chamber by an ion conductor and the oxygen feeder, modifying drift of NOx concentration by oxygen concentration or heating the ion conductor and an oxygen feeder. The ion conductor has the first and second electrodes attached thereto in the measuring chamber. The first electrode is active for oxygen and NOx gas, the second electrode is active for oxygen. The oxygen feeder is disposed to face the first electrode and second electrode.

The nitrogen oxide detector according to the present invention comprises an ion conductor; a first electrode secured to the ion conductor, and being active for oxygen and NOx gas; a second electrode secured to the ion conductor, and being active for oxygen; and an oxygen feeder disposed to face the first electrode and second electrode and define a measuring chamber with the first electrode and second electrode for supplying oxygen to the measuring chamber. Test gas that contains NOx and interference gas is supplied to the measuring chamber so that the interference gas is oxidized by oxygen or oxygen ion supplied to the measuring chamber through the oxygen feeder to detect a total amount of NOx in the test gas based on a level of EMF produced between the first and second electrodes.

In an embodiment of the invention, the first electrode has an oxide electrode and a collector. The oxide electrode is formed by a layer of compound oxide or oxides of transition metal or metals active for oxygen and NOx gas, and the collector is formed of platinum. An catalytic layer may be provided to support oxidation catalyst in the measuring chamber. The first electrode exposed to the test gas has its selectivity to nitrogen oxide and oxygen, and the second electrode exposed to the test gas has its lower selectivity to nitrogen oxide than that of the first electrode and its substantially equal selectivity to oxygen to that of the first electrode. The oxygen feeder includes an oxygen ion conductor, a cathode attached to one side of the oxygen ion conductor, and an anode in the measuring chamber and attached to the other side of the oxygen ion conductor to supply the test gas with oxygen ion or active oxygen in the measuring chamber. Also, a reference electrode is provided in the ion conductor for exposure to atmospheric air or atmosphere of its constant oxygen content isolated from the test gas. The oxygen feeder has its capacity to supply a surplus amount of oxygen over oxidation equivalent of reducing gas in the test gas. The anode of oxygen feeder is formed of noble metal or metals of oxidation catalyst ability selected from a group of platinum (Pt), palladium (Pd), iridium (Ir), silver (Ag) or their alloy or alloys or complex of these metals and metal oxide. The anode has two layered structure inclusive of oxidation catalytic layers. The test gas flows to the first electrode through the porous anode in the oxygen feeder or the porous catalytic layer in contact with the anode. Heating means is provided for heating the ion conductor and oxygen feeder.

The above-mentioned as well as other objects of the present invention will become apparent during the course of the following detailed description and appended claims.

DETAILED DESCRIPTION OF THE INVENTION

Figure 1:
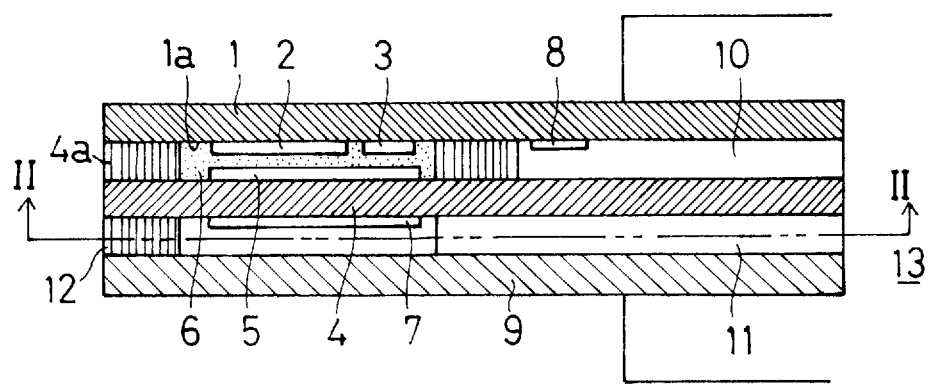
FIG. 1 is a sectional view of a nitrogen oxide detector according to the present invention.
Figure 2:
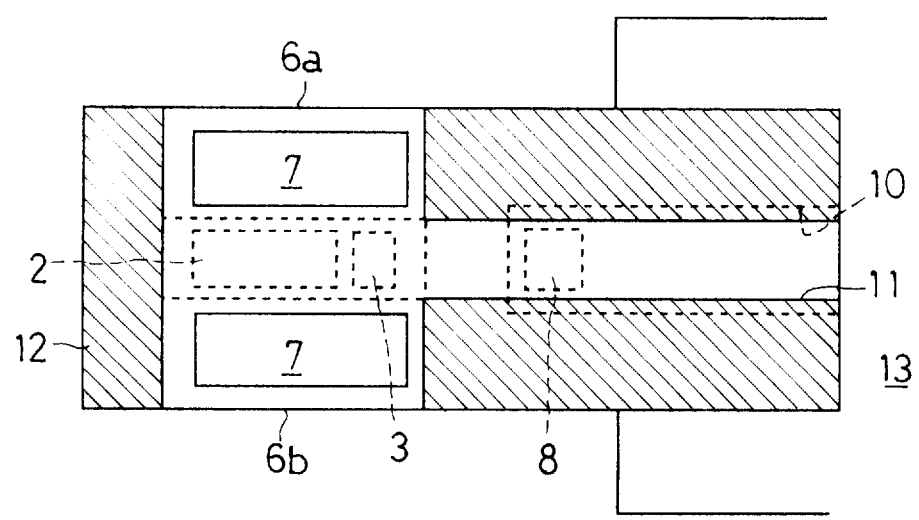
FIG. 2 is a sectional view taken along a II—II line of FIG. 1.

FIG. 1 shows a basic constitution of the nitrogen oxide detector according to the present invention. The nitrogen oxide detector comprises an ion conductor 1; an oxygen feeder 4 attached to the ion conductor 1 through oxygen ion conductors 4a to face the ion conductor 1; a ceramic substrate 9 secured to the oxygen feeder 4 through spacers 12; first and second electrodes 2 and 3 in a measuring chamber 1a defined by the ion conductor 1, oxygen ion conductors 4a and oxygen feeder 4.

The oxygen feeder 4 comprises the oxygen ion conductor 4a; an anode 5 attached to the oxygen feeder 4 in the measuring chamber 1a; and a cathode 7 attached to the oxygen feeder 4 in a passage 11 defined by the oxygen feeder 4, spacers 12 and ceramic substrate 9 for communication with atmosphere 13. The first and second electrodes 2 and 3 are disposed in spaced relation to each other, and face the anode 5 with a small gap in the measuring chamber 1a formed between the first and second electrodes 2 and 3 and anode 5. The oxygen feeder 4, anode 5 and cathode 7 serve as an oxygen pump which supplies oxygen in the passage 11 through the cathode 7, oxygen feeder 4 and anode 5 into the measuring chamber 1a. To this end, the cathode 7 is formed of a material superior in ionization of oxygen, and positioned to face the ceramic substrate 9 with a space in the passage 11. The measuring chamber 1a is filled with a porous catalytic layer 6 which carries oxidation catalyst and forms a diffusion path for test gas. The catalytic layer 6 has two side surfaces 6a and 6b opposite with each other either of which is exposed to exhaust gas discharged from engine so that test gas flows by diffusion from the side surfaces 6a and 6b through the catalytic layer 6 and porous anode 5 into the measuring chamber 1a to thereby expose the first and second electrodes 2 and 3 to same test gas in the measuring chamber 1a through the catalytic layer 6. The anode 5 is disposed in the vicinity of the side surfaces 6a and 6b upstream the first electrode 2 along the diffusion path of test gas. Not shown but, the first electrode 2 comprises an oxide electrode with a layer of compound oxide or oxides of transition metal or metals active for oxygen and NOx gas and a collector of platinum so that the first electrode 2 is active for oxygen and NOx gas. The second electrode 3 is formed of platinum active for oxygen in substantially equivalent grade of sensitivity for oxygen, however, the second electrode 3 has the different chemical activity of catalyst for NOx gas from that of the first electrode 2. Therefore, the second electrode 3 does not necessarily utilize its materials substantially homogeneous to those of the first electrode 2. Also, provided in the ion conductor 1 is a reference electrode 8 which opens to a hole 10 formed between the ion conductor 1 and oxygen feeder 4 for exposure of the reference electrode 8 to atmospheric air or atmosphere of a certain oxygen concentration through the hole 10.

The ion conductor 1 may contain for example yttria-stabilized zirconia typically used as an oxygen ion conductor. The first electrode 2 has sensibilities for nitrogen oxide and oxygen, whereas the second electrode 3 has its inferior sensibility for nitrogen oxide than that of the first electrode 2 but the second electrode 3 has its sensibility for oxygen in substantially same level as that of the first electrode 2 to detect NOx concentration by the level of EMF produced between the first and second electrodes 2 and 3.

The oxygen feeder 4 has its capacity enough to supply oxygen ion or active oxygen in test gas in the measuring chamber 1a in an excessive amount of oxygen greatly over the oxidation equivalent of reducing gases in test gas to exclude interference gas such as typically hydrocarbon gas or carbon monoxide gas in test gas of the measuring chamber 1a by oxidization of the interference gas with oxygen or oxygen ion supplied by the oxygen feeder 4 without disadvantageous fluctuation in outputs of the sensor resulted from insufficient amount of supplied oxygen in the vicinity of the oxidation equivalent. The oxygen ion conductor 4a of the oxygen feeder 4 is disposed in the diffusion path of test gas supplied to the first electrode 2 so that it operates as an oxygen pump by applying voltage of a constant level between the anode 5 and cathode 7 of the oxygen feeder 4. In this case, arranged in the diffusion path of the test gas connected with the first electrode 2 is the anode 5 which supplies oxygen ion or active oxygen in the measuring chamber 1a. The oxygen feeder 4 is not restrictive to supply an excessive amount of oxygen greatly over oxidation equivalent of reducing gas in test gas or NO gas because the excessive amount of oxygen exerts no influence on detection of nitrogen oxide by deducting output of the second electrode 3 from output of the first electrode 2 for cancellation of interference by oxygen. Accordingly, no influence is exerted on detection of nitrogen oxide by fluctuation of oxygen content in test gas in contact to the first and second electrodes 2 and 3. The oxygen feeder 4 has its capacity that can provide oxygen in an amount necessary for full oxidization of interference gases in test gas, and there is no need for restriction of supplying oxygen from the oxygen feeder 4 during operation of the oxygen feeder 4 unlike a semiconductor sensor which requires restriction of oxygen amount supplied to the atmosphere in which the semiconductor sensor is located. The anode 5 of the oxygen feeder 4 is preferably formed of noble metal or metals of oxidation catalyst ability selected from a group of platinum (Pt), palladium (Pd), iridium (Ir), silver (Ag) or their alloy or alloys or complex of these metals and metal oxide. The anode 5 may comprise an additional oxidation catalytic layer in contact to a main structure of the anode 5 made of gold (Au) or other electrically conductive metal or metals. Also, the anode 5 may have a two layered structure inclusive of oxidation catalytic layers.

In the nitrogen oxide detector according to the present invention, the anode 5 of the oxygen feeder 4 may be formed of noble metal or metals of high activity for oxidation catalyst selected from a group of platinum (Pt), palladium (Pd), iridium (Ir) or alloy or alloys of these metals. Otherwise, catalyst of high activity may be layered on the electrode of the anode 5. Vaporized oxygen molecules are supplied from the anode 5 of delivery outlet, and oxygen ions or oxygen molecules are adsorbed on an electrode surface of the anode 5 or a solid phase surface in contact to the electrode surface. It has been found that oxygen ions or oxygen molecules on the electrode surface of the anode 5 or the solid phase surface have greater chemical activity than that of vaporized oxygen molecules. Accordingly, oxygen ion or oxygen molecules adsorbed on the surfaces of the anode 5 and catalytic layer 6 are bonded with interference whereas the anode 5 of the oxygen feeder 4 simply supplies molecular oxygen or gaseous oxygen. In this case, adsorbed oxygen on the surfaces of the anode 5 and catalytic layer 6 can utilize supplied oxygen more effectively than oxygen supplied from the anode 5.

To still more effectively utilize oxygen, porosity of the anode 5 or catalytic layer 6 for providing the path of test gas may be adjusted to provide diffusion resistance of test gas in a desired level so that interference gas facilitates to react with oxygen supplied from the anode 5 and adsorbed on the surfaces of the anode 5 and catalytic layer 6 to accelerate oxidation of the interference gas.

In detecting nitrogen oxide contained in test gas, the nitrogen oxide detector is attached within an exhaust pipe of an internal combustion engine to expose the side surfaces 6a and 6b of the catalytic layer 6 to exhaust gas as test gas in the exhaust pipe so that the hole 10 and passage 11 of the detector are communicated with atmospheric air. Accordingly, test gas flows by diffusion from the side surfaces 6a and 6b, porous catalytic layer 6 and porous anode 5 into the measuring chamber 1a to expose the first and second electrodes 2 and 3 to test gas that may contain NOx and interference gases. On the other hand, voltage of a predetermined level is applied between the anode 5 and cathode 7 of the oxygen feeder 4 to operate the oxygen pump formed by the oxygen feeder 4, anode 5 and cathode 7. Interference gases contained in test gas are oxidized to inactive water or carbon dioxide with oxygen ions or active oxygen supplied from the oxygen feeder 4 into the measuring chamber 1a when interference gas passes through the anode 5 and catalytic layer 6, thus to remove interference gas from test gas.

Exhaust gas usually contains a major amount of NO and $NO_2$ and small amount of $N_2O$, $N_2O_3$ and $N_2O_5$. Therefore, NOx contained in test gas comprises NO, $NO_2$ and remainders. When the first electrode 2 detects the major amount of $NO_2$ and NO in test gas, it generates a positive (+) output upon contact with $NO_2$, and it generates a negative (−) output upon contact with NO so that the negative output by NO inconveniently cancels the positive output by $NO_2$ thus to prevent exact detection of NOx if NO is not oxidized. Accordingly, NO and $NO_2$ gases are considered as interfering with each other in output of the first electrode 2 because the polarities of output from the detector are opposite from each other to produce EMF of reverse directions in contact of the first electrode 2 with NO and $NO_2$ gases.

Although test gas contains NO and $NO_2$ gases, interference by NO gas can be avoided because it is oxidized to $NO_2$ gas by bonding NO gas with oxygen ions or active oxygen fed from the oxygen feeder 4. The first electrode 2 produces a positive output upon contact with the total amount of $NO_2$ which is the substantial sum of NOx contained in test gas so that a total amount of NOx gas can be detected as a total amount of $NO_2$. When test gas that contains NOx gas contacts the first and second electrodes 2 and 3, the first electrode 2 detects chemical potentials of oxygen produced from $NO_2$ gas and oxygen contained in test gas, and the second electrode 3 detects a single chemical potential of oxygen contained in test gas so that NOx gas can be detected by EMF produced between the first and second electrodes 2 and 3. Since the potential difference is measured between electric potentials of the first and second electrodes 2 and 3 to detect the amount of NOx gas, the influence by oxygen can be cancelled. Then, the detected output is free from oxygen gas content in test gas without interference by oxygen gas.

Test gas is introduced into the measuring chamber 1a along the diffusion path from the side surfaces 6a and 6b through the anode 5 to the first electrode 2. In this case, it would be preferable to form one way flow path for test gas through the catalytic layer 6 to the first electrode 2 and to provide the anode 5 of the oxygen feeder 4 along the diffusion path. The cathode 7 is preferably mounted in the passage 11 communicated with atmospheric air, however, it may be exposed to test gas atmosphere if the test gas contains sufficient oxygen.

If NOx gas, mainly containing $NO_2$, cannot be detected with full accuracy due to influence of oxygen which causes degradation of accuracy in detection, a reference electrode 8 may be provided on the ion conductor 1 which supports the first and second electrodes 2 and 3 to expose the reference electrode 8 to atmospheric air or atmosphere of a constant oxygen content isolated from test gas. With increase of oxygen content, less amount of EMF is produced between the first and second electrodes 2 and 3 due to the shift of the equilibrium potential to $NO_2$ production side with a large amount of oxygen content in the measuring chamber 1a, although a little amount of oxygen content exerts almost no influence on the detection. Accordingly, increase of oxygen content causes reduction of EMF and degradation of detection accuracy. In this case, oxygen content can exactly be detected by EMF produced between the second electrode 3 and reference electrode 8 communicated with atmospheric air or atmosphere of constant oxygen content because the resultant EMF precisely corresponds to oxygen concentration around the second electrode 3 so that outputs of NOx from the detector can be modified to cancel the drift of NOx concentration by oxygen concentration. However, such a reference electrode 8 is not necessarily required because dissociation equilibrium of $NO_2$ gas exists with a much higher concentration of oxygen, and therefore, usually the detector does not raise a problem of compensation by the reference electrode 8.

To operate the ion conductor 1 and oxygen feeder 4 in their good condition, it is necessary to heat them at optimum temperatures of their components, however, alternatively they may be heated by exhaust gas employed as test gas or ambient gas of high temperature. Also, the detector may be equipped with self-heating means or integrated heater to heat it at a predetermined elevated temperature for optimum operation. In the embodiment shown in FIG. 1, the ceramic substrate 9 may comprise an embedded heater therein so that it may be attached to the oxygen feeder 4 through spacers 12 to form the passage 11. Also, a film thermocouple may be formed on a surface of the ion conductor 1 or ceramic substrate 9 for example by a screen printing method for feedback control of the detector temperature. Otherwise, outputs from the detector may be corrected based on output signals of temperatures of the detector and test gas.

The present invention is not limited to the structure of the embodiment exemplified in FIG. 1, and various variations can naturally be added to the embodiment in connection with arrangement, configuration, elements and materials. Of course, the ion conductor 1 and the first and second electrodes 2 and 3 are not limited to the foregoing materials and structures so far as they meet the scope of claims.

To prepare samples of the nitrogen oxide detector according to the present invention, three zirconia substrates for an ion conductor 1, oxygen feeders 4 and ceramic substrate 9 were made of stabilized zirconia with 8 mol % yttria of 0.25 mm×5 mm ×50 mm. The first zirconia substrate were disposed within a RF sputtering device and a $NiCr_2O_4$ layer was formed on the first zirconia substrate by sputtering in an atmosphere of mixed gas of argon and oxygen. Then, platinum (Pt) paste was applied on the $NiCr_2O_4$ layer and on two areas of the first zirconia substrate by screen printing method to form the ion conductors 1 which have a first electrode 2 of the $NiCr_2O_4$ layer and platinum, a second electrode 3 of platinum and a reference electrodes 8 of platinum. Also, platinum paste was applied on two areas of top and bottom surfaces of the second zirconia substrate to form the oxygen feeder 4. The first, second and third zirconia substrates were burned in a heating furnace. Subsequently, a $Bi_2O_3$ layer was provided on the platinum area of the top surface of the second zirconia substrate to form an anode 5 of the oxygen feeder 4. Then, an alumina heating plate with a platinum-embedded heater was attached to the third zirconia substrate so that the alumina plate faces the cathode 7 of the oxygen feeder 4. These three zirconia substrates were attached to each other together with the oxygen ion conductors 4a and spacers 12 by glass glue of high melting point into a structure shown in FIG. 1 so that the oxygen feeder 4 and ceramic substrate 9 were secured with a gap therebetween to form a passage 11 communicated with atmospheric air. Also, the alumina heating plate with the heater was exposed to spheric air, and thus the nitrogen oxide detector was obtained.

In use, the nitrogen oxide detector was heated by applying electric voltage on the alumina heating plate approximately at a temperature of 650° C. Voltage of DC 1 V was applied between the anode 5 and cathode 7 to activate the oxygen feeder 4. Following Table 1 indicates a test result of the invention's detectors with the oxygen feeder 4 and comparative detectors without oxygen feeder.

Table 1 shows a result in evaluating performance of the nitrogen oxide detector according to the present invention by utilizing test gases of constant concentration: 50ppm of 4% oxygen gas ($O_2$) and balance nitrogen gas ($N_2$). As understood from Example Nos. 4, 5, 6 and 8, harmful influence of interference gas such as hydrocarbon gas or NO gas can obviously be avoided by oxidation of the interference gas with oxygen supplied through the oxygen feeder 4.

TABLE 1

| No | Test gas | Interference Gas | Oxygen Feeder | Detector Output | Interference Generation |
|---|---|---|---|---|---|
| 1 | $NO_2$ | Not introduced | Unworked | 62 mV | |
| 2 | NO | Not introduced | Unworked | −30 mV | |
| 3 | $NO_2$ | $C_3H_6$ 50 ppm | Unworked | 41 mV | Yes |
| 4 | $NO_2$ | $C_3H_6$ 50 ppm | Worked | 58 mV | No |
| 5 | $NO_2$ | NO 50 ppm | Unworked | 51 mV | Yes |
| 6 | $NO_2$ | NO 50 ppm | Worked | 65 mV | No |
| 7 | NO | $C_3H_6$ 50 ppm | Unworked | −22 mV | Yes |
| 8 | NO | $C_3H_6$ 50 ppm | Worked | −27 mV | Slight |

Current flow of approximately 100 mV of EMF was produced between the second electrode 3 and reference electrode 8 due to the difference in oxygen concentration between test gas with oxygen content of approximately 0% and air with oxygen content of approximately 20.9%. Accordingly, it is apparent that EMF produced between the second electrode 3 and reference electrode 8 is available as an indication value of oxygen concentration in test gas.

The nitrogen oxide detector according to the present invention is suitable for detection of nitrogen oxide content with interference gases, in particular, exhaust gas from engine. This detector can also sense degradation or abnormal operation of clarification system for exhaust gas with catalyst and an air/fuel ratio sensor by detecting the amount of $NO_2$ in exhaust gas

TABLE 2

| No | Test gas 50 ppm | Interference Gas | Oxygen Feeder | Detector Output | Detection of NOx in Total Amount |
|---|---|---|---|---|---|
| 9 | $NO_2$ | Not introduced | Unworked | 58 mV | |
| 10 | NO | Not introduced | Unworked | −26 mV | |
| 11 | $NO_2$ | Not introduced | Worked | 60 mV | |
| 12 | NO | Not introduced | Worked | 56 mV | |
| 13 | NO | NO 50 ppm | Unworked | 38 mV | Undetected |
| 14 | $NO_2$ | NO 50 ppm | Worked | 66 mV | Detected |
| 15 | $NO_2$ | NO 50 ppm $C_3H_6$ 50 ppm | Worked | 65 mV | Detected Without Interference |

In this way, the detector of the invention can avoid influence of interference gas by oxidizing it with oxygen or oxygen ion and also by detecting the amount of NOx in view of level of EMF produced between the first electrode 2 for detecting oxygen and NO2 gas and the second electrode 3 for detecting oxygen.

Additional samples of the nitrogen oxide detector similar to those of the foregoing embodiment were prepared and worked in different modes from the foregoing embodiment to evaluate the detection property of the oxygen feeder 4. Table 2 indicates the result of the evaluation. As understood from Table 2, the invention's nitrogen oxide detectors were never susceptible to any interference gas of negative output as especially shown by Sample No. 14, and the detectors showed detection outputs of NO test gas similar to $NO_2$. Obviously, these test results demonstrate that the invention's nitrogen oxide detector can exactly detect a total amount of NOx.

Worked mode of this invention is not limited to the foregoing embodiment, and various modifications can be made in the embodiment. For example, in lieu of the catalytic layer 6, the measuring chamber 1a may be filled up with the anode 5.

The nitrogen oxide detector according to the instant invention can give rise to the following features:

(1) The detector can accurately detect the amount of nitrogen oxide.

(2) The detector can exactly be operated at an elevated temperature.

(3) Interference by interference gases such as hydrocarbon gas or NO gas can be evaded for accuracy detection of nitrogen oxide.

(4) The detector can be directly inserted into exhaust gas of a high temperature.

(5) The detector can be manufactured in small size and with simple structure.

What is claimed is:

1. A method for detecting nitrogen oxide in test gas comprising the steps of:

supplying, into a measuring chamber, test gas that contains NOx and at least an interference gas;

oxidizing said interference gas and NO gas in the test gas by oxygen or oxygen ion supplied to said measuring chamber through an oxygen feeder; and detecting a total amount of NOx in the test gas based on a level of EMF produced between a first electrode for detecting oxygen and $NO_2$ gas and a second electrode for detecting oxygen.

2. The method of claim 1, further comprising defining said measuring chamber by an ion conductor and said oxygen feeder, said ion conductor having said first and second electrodes attached thereto in said measuring chamber, said first electrode being active for oxygen and NOx gas, said second electrode being active for oxygen, and said oxygen feeder being disposed to face said first electrode and second electrode.

3. The method of claim 2, further comprising heating said ion conductor and an oxygen feeder.

4. The method of claim 1, further comprising modifying drift of NOx concentration by oxygen concentration.

5. A nitrogen oxide detector comprising:

an ion conductor, a first electrode secured to said ion conductor, and being active for oxygen and NOx gas, a second electrode secured to said ion conductor, and being active for oxygen, and an oxygen feeder disposed to face said first electrode and second electrode and define a measuring chamber with said first electrode and second electrode for supplying oxygen to said measuring chamber, wherein test gas that contains NOx and interference gas is supplied to said measuring chamber so that said interference gas is oxidized by oxygen or oxygen ion supplied to said measuring chamber through said oxygen feeder to detect a total amount of NOx in the test gas based on a level of EMF produced between said first and second electrodes.

6. The nitrogen oxide detector of claim 5, wherein said first electrode has an oxide electrode and a collector.

7. The nitrogen oxide detector of claim 6, wherein said oxide electrode is formed by a layer of compound oxide or oxides of transition metal or metals active for oxygen and NOx gas; said collector is formed of platinum (Pt).

8. The nitrogen oxide detector of claim 5, further comprising an catalytic layer which supports oxidation catalyst in said measuring chamber.

9. The nitrogen oxide detector of claim 8, including a means for flowing said test gas to said first electrode through said porous anode in said oxygen feeder or through said porous catalytic layer in contact with said anode.

10. The nitrogen oxide detector of claim 5, wherein said first electrode exposed to the test gas has its selectivity to nitrogen oxide and oxygen;

said second electrode exposed to the test gas has its lower selectivity to nitrogen oxide than that of said first electrode and its substantially equal selectivity to oxygen to that of said first electrode.

11. The nitrogen oxide detector of claim 5, wherein said oxygen feeder includes an oxygen ion conductor, a cathode attached to one side of said oxygen ion conductor, and an anode in said measuring chamber and attached to the other side of said oxygen ion conductor to supply the test gas with oxygen ion or active oxygen in the measuring chamber.

12. The nitrogen oxide detector of claim 11, wherein said anode of oxygen feeder is formed of noble metal or metals of oxidation catalyst ability selected from a group consisting of platinum (Pt), palladium (Pd), iridium (Ir), silver (Ag) and alloys, complexes and metal oxides of these metals.

13. The nitrogen oxide detector of claim 11, wherein said anode has a two layered structure inclusive of oxidation catalytic layers.

14. The nitrogen oxide detector of claim 5, further comprising a reference electrode in said ion conductor for exposure to atmospheric air or atmosphere of its constant oxygen content isolated from the test gas.

15. The nitrogen oxide detector of claim 5, wherein said oxygen feeder has its capacity to supply a surplus amount of oxygen over oxidation equivalent of reducing gas in the test gas.

16. The nitrogen oxide detector of claim 5, further comprising heating means for heating said ion conductor and oxygen feeder.

* * * * *